(12) United States Patent
Maadi et al.

(10) Patent No.: US 8,348,663 B2
(45) Date of Patent: Jan. 8, 2013

(54) DENTAL DEVICE FOR TEMPORARILY FILLING THE TOOTHLESS GAP FOLLOWING THE EXTRACTION OF A TOOTH AND METHOD FOR USING SAID DEVICE

(75) Inventors: Mahfoud Maadi, Mulhouse (FR);
Abd-Al-Qadir Maadi, Mulhouse (FR);
Karim Maadi, Mulhouse (FR)

(73) Assignee: Dynadent Sarl, Mulhouse (FR)

( * ) Notice: Subject to any disclaimer, the term of this patent is extended or adjusted under 35 U.S.C. 154(b) by 0 days.

(21) Appl. No.: 13/126,536

(22) PCT Filed: Oct. 30, 2009

(86) PCT No.: PCT/FR2009/001264
§ 371 (c)(1),
(2), (4) Date: Apr. 28, 2011

(87) PCT Pub. No.: WO2010/049612
PCT Pub. Date: May 6, 2010

(65) Prior Publication Data
US 2011/0207080 A1    Aug. 25, 2011

(30) Foreign Application Priority Data
Oct. 30, 2008  (FR) ..................... 08 06030

(51) Int. Cl.
*A61C 13/107* (2006.01)

(52) U.S. Cl. .......................... 433/7; 433/178

(58) Field of Classification Search .............. 433/7, 172, 433/177, 178, 181
See application file for complete search history.

(56) References Cited

U.S. PATENT DOCUMENTS

| 618,105 | A | * | 1/1899 | Knapp ............................. 433/7 |
| 3,854,210 | A |   | 12/1974 | Franklin et al. |
| 4,163,318 | A |   | 8/1979 | Tigani |
| 4,431,415 | A | * | 2/1984 | Tigani ........................ 433/172 |
| 4,609,355 | A | * | 9/1986 | Harvey et al. ................ 433/181 |
| 4,661,067 | A | * | 4/1987 | Harvey et al. ................ 433/181 |
| 5,439,377 | A | * | 8/1995 | Milanovich ..................... 433/7 |
| 6,783,361 | B2 | * | 8/2004 | Huge et al. ...................... 433/7 |

FOREIGN PATENT DOCUMENTS
EP        2 055 262 A2    5/2009

* cited by examiner

*Primary Examiner* — Ralph Lewis
(74) *Attorney, Agent, or Firm* — David & Bujold, PLLC (57) ABSTRACT

A dental device (10) for temporarily filling a toothless gap (50) following extraction of a tooth. The dental device is arranged so as to be located in a space between two adjacent teeth (30, 40) bordering, on each opposed side, the toothless gap. The dental device comprises a central block (11) and two arms (12, 13) located on opposite sides of the central block (11). The two arms (12, 13) are extendible between a retracted position and an extended position. Each arm carries, at a free end thereof, at least one support (14, 15) adapted for resting respectively on a surface of the adjacent teeth when the arms are in the extended position. The central block includes an adjusting mechanism (19) for moving the two arms into the extended position, and a lock (20, 21, 22) locks the adjusting mechanism when the arms are in the extended position.

18 Claims, 8 Drawing Sheets

DENTAL DEVICE FOR TEMPORARILY FILLING THE TOOTHLESS GAP FOLLOWING THE EXTRACTION OF A TOOTH AND METHOD FOR USING SAID DEVICE

This application is a National Stage completion of PCT/FR2009/001264 filed Oct. 30, 2009, which claims priority from French patent application serial no. 08/06030 filed Oct. 30, 2008.

FIELD OF THE INVENTION

The present invention relates to a dental device for temporarily filling the toothless gap following the extraction of a tooth, this device being arranged so as to be put in place in a space located between two adjacent teeth bordering the toothless gap and comprising a central block and two arms opposite to each other, extensible between a retracted position and an extended position, each of these arms carrying at their free end at least one support adapted for resting respectively on a surface of the adjacent teeth when the arms are in the extended position, and the central block including an adjusting mechanism arranged for bringing the opposite arms into the extended position.

The invention also relates to a method for using this dental device.

BACKGROUND OF THE INVENTION

When extracting a tooth, in particular following a non-scheduled extraction or following a trauma, the gaps between the neighbouring teeth are generally filled temporarily with a unit prosthesis fastened with the help of cumbersome hooks, which are bothersome for the patient and visible, or with a bridge, which has the drawback of requiring the reduction of the supporting teeth to allow the realization of a part comprising three teeth. The goal of these temporary elements is to ensure a functional rehabilitation, to improve the aesthetic presentation by filling the toothless gap created by the extraction and to enhance the progress of the bone healing.

The major drawback of the temporary bridges and unit prostheses stems from the fact that these elements cannot be produced in only one work session, which would take place immediately after the extraction. In fact, they must be manufactured by dental-prosthesis technicians working on the base of an impression made by the dentist. These various operations require at least two work sessions for the dentist, between the moment when he extracts the tooth and makes the impression and the moment when he can put the temporary element, which has been manufactured in the meantime by the workshop of the prosthesis-maker, in place in the mouth of the patient. Assuming that the element has been properly manufactured and that it requires no or only little adjusting, the dentist requires at least two sessions of intervention with the patient.

Furthermore, the attached partial prosthesis or the removable unit prosthesis has further drawbacks. It requires a large volume in the mouth, it generates a loss of adaptation as the healing progresses, it has a relatively high mobility and creates aesthetic damage due to the fact that the hooks are visible, which is often considered as a handicap by the patient or the people around him.

The temporary unit bridges require cutting to shape the teeth adjacent to the toothless gap, which is unacceptable when these teeth are healthy. In fact, such a cutting to shape leads to the voluntary mutilation of healthy teeth to allow putting in place a temporary accessory. In addition, this solution is particularly expensive for the patient.

The publication U.S. Pat. No. 4,163,318 describes a device for filling the space between two teeth comprising two extensible arms moved by a central pinion meshing two opposite racks, the central pinion being mobile in rotation in a support by means of a driving screw. This device has the drawback of being invasive, since the ends of the extensible arms are inserted in seats cut in the healthy teeth. It is relatively expensive since it requires accuracy in the micron range. Furthermore, it comprises no mechanical locking means for the arms in extended position that would prevent the risk of loosening or misadjusting of the device. This device is thus not satisfying.

SUMMARY OF THE INVENTION

The present invention brings a solution for the above-mentioned problems by offering a non-invasive device, enabling the immediate temporary placement of a bridge, after the extraction of a tooth, to respect the constraints imposed so that the healing of the wound can take place in the best conditions, to offer the patient a flawless aesthetics and to reduce the costs by limiting the number of persons intervening and the number of interventions.

To that purpose, the dental device according to the invention is characterized in that the adjusting mechanism comprises two loop-shaped adjustable straps arranged to surround respectively the adjacent teeth and to bring the arms in the extended position, and in that the device comprises means for locking the straps when the arms are in the extended position.

The straps are preferably flexible and can be made out of fiberglass.

So this dental device is non-invasive and can be adapted in situ to any type of teeth thanks to its two adjustable straps that surround the teeth adjacent to the toothless gap and allow rigidly fastening the device between these teeth by tightening these straps with the adjusting and locking means in order to extend the arms and press the supports against these teeth. This device allows immediate placement of a bridge in the patient, without preparatory laboratory work requiring the making of an impression.

In a preferred embodiment, the adjusting mechanism comprises a reverse-lock device that may have at least one toothed wheel cooperating with pawls.

In the preferred embodiment, each of the straps advantageously comprises an end that is attached to one of the extensible arms and the other end is attached to a rotary shaft of the adjusting mechanism, this rotary shaft carries actuating means and the toothed wheel of the reverse-lock device.

Preferably, the central block comprises a housing containing the pawls, arranged to receive the rotary shaft. It is preferably at least partly hollowed and arranged to receive a photo or chemo-polymerizable composite resin in order to lock the adjusting mechanism in position when the arms are in the extended position.

In an embodiment variant, the adjusting mechanism can include at least one return element accommodated in the central block and arranged to exert a force on the arms towards the extended position.

In this case, each of the straps can comprise an end attached to one of the extensible arms while the other end cooperates with a locking mechanism.

This locking mechanism can comprise at least one blocking element that cooperates with each arm in order to lock the corresponding strap by pinching it between the arm and the locking element. This locking element advantageously comprises at least one locking tab that is arranged to be locked on the corresponding arm.

Also to this purpose, the method for using the dental device according to the invention is characterized in that one positions the dental device between two adjacent teeth that border a toothless gap, one positions the straps around the two adjacent teeth, one actuates the adjusting mechanism to extend the opposite arms until the supports come into contact with the adjacent surfaces of the adjacent teeth, and one tightens the straps around the teeth. When the tightening is considered sufficient, one can lock the dental device in position with a photo or chemo-polymerisable resin arranged to lock the adjusting mechanism.

BRIEF DESCRIPTION OF THE DRAWINGS

The present invention and its advantages will be better revealed in the following description of an embodiment given as a non limiting example, in reference to the drawings in appendix, in which.

DETAILED DESCRIPTION OF THE PREFERRED EMBODIMENTS

With reference to FIGS. 1 to 6, the dental device 10 comprises a central block 11 carrying two extensible arms 12 and 13 located opposite to each other, having respectively, at their free end, supports 14 and 15 whose shape is approximately that of cylindrical segments. One will note that each support 14 and 15 can be made in one single element or in two or more elements connected to the respective arms 13 and 12. Two loop-shaped straps 16 and 17 are respectively associated with the two supports 14 and 15, these straps being intended for surrounding the adjacent teeth of a toothless gap. The central block 11 comprises a tubular element 18 arranged for carrying both arms 12 and 13 and for allowing them to slide axially for their extension as from a retracted initial position. In this instance, the arm 13 has an external cross-section approximately equal to the internal cross-section of the tubular element 18 and slides inside of the latter and the arm 12 has an internal cross-section approximately equal to the external cross-section of the tubular element 18 and slides outside of the latter. The movement of the arm 12 is guided by two protruding pins 11a located opposite to each other, attached to the central block 11 and inserted in two lateral notches 12a of the arm 12. The pins 11a protrude with respect to the external surface of the central block 11. The movement of the arm 13 is guided by two protruding pins (not represented) attached to the central block 11 and inserted in two lateral notches 13a of the arm 13. These pins protrude with respect to the internal surface of the central block 11.

Figure 1:
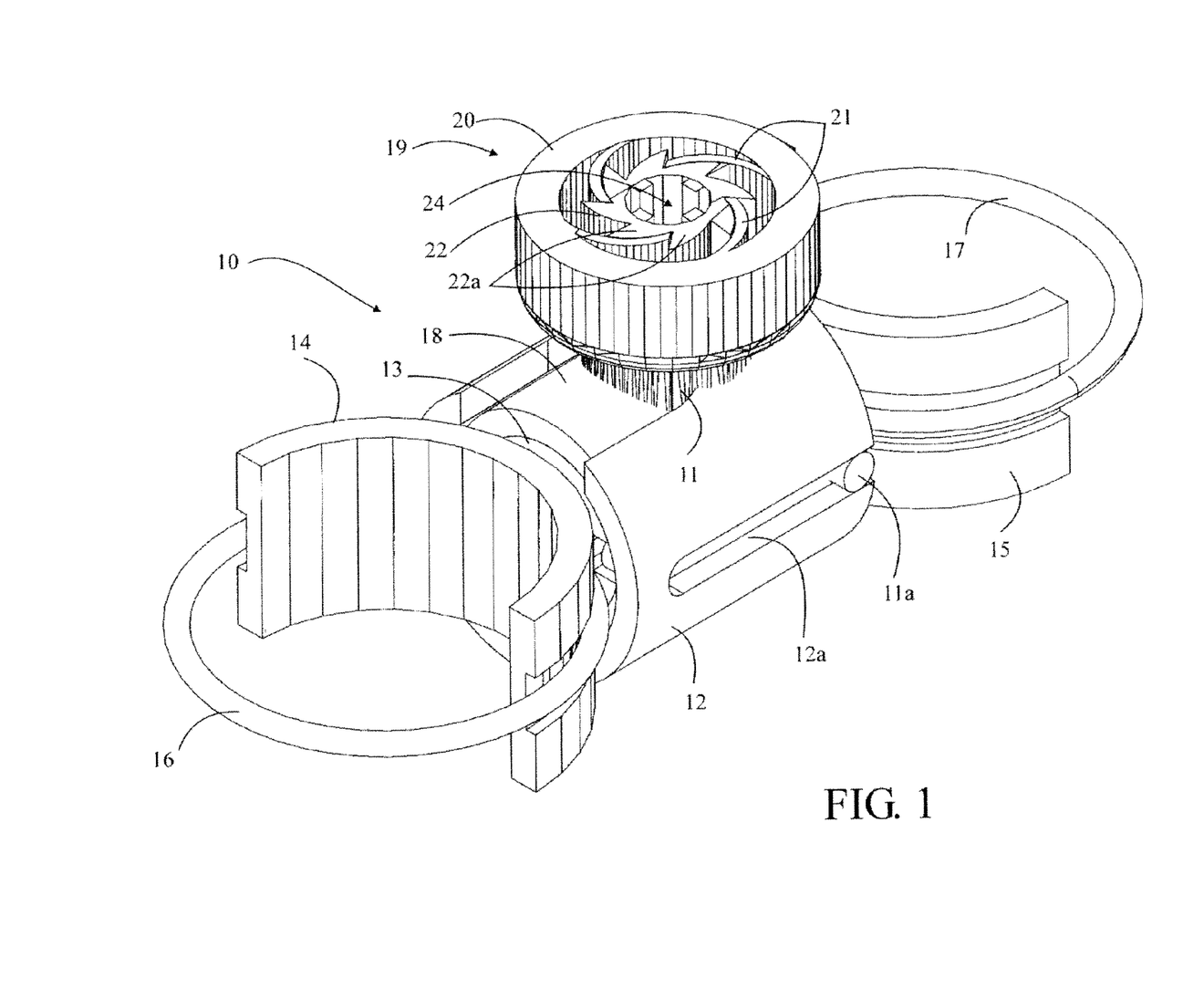
FIG. 1 represents a perspective view of an embodiment of the dental device according to the invention.
Figure 2:
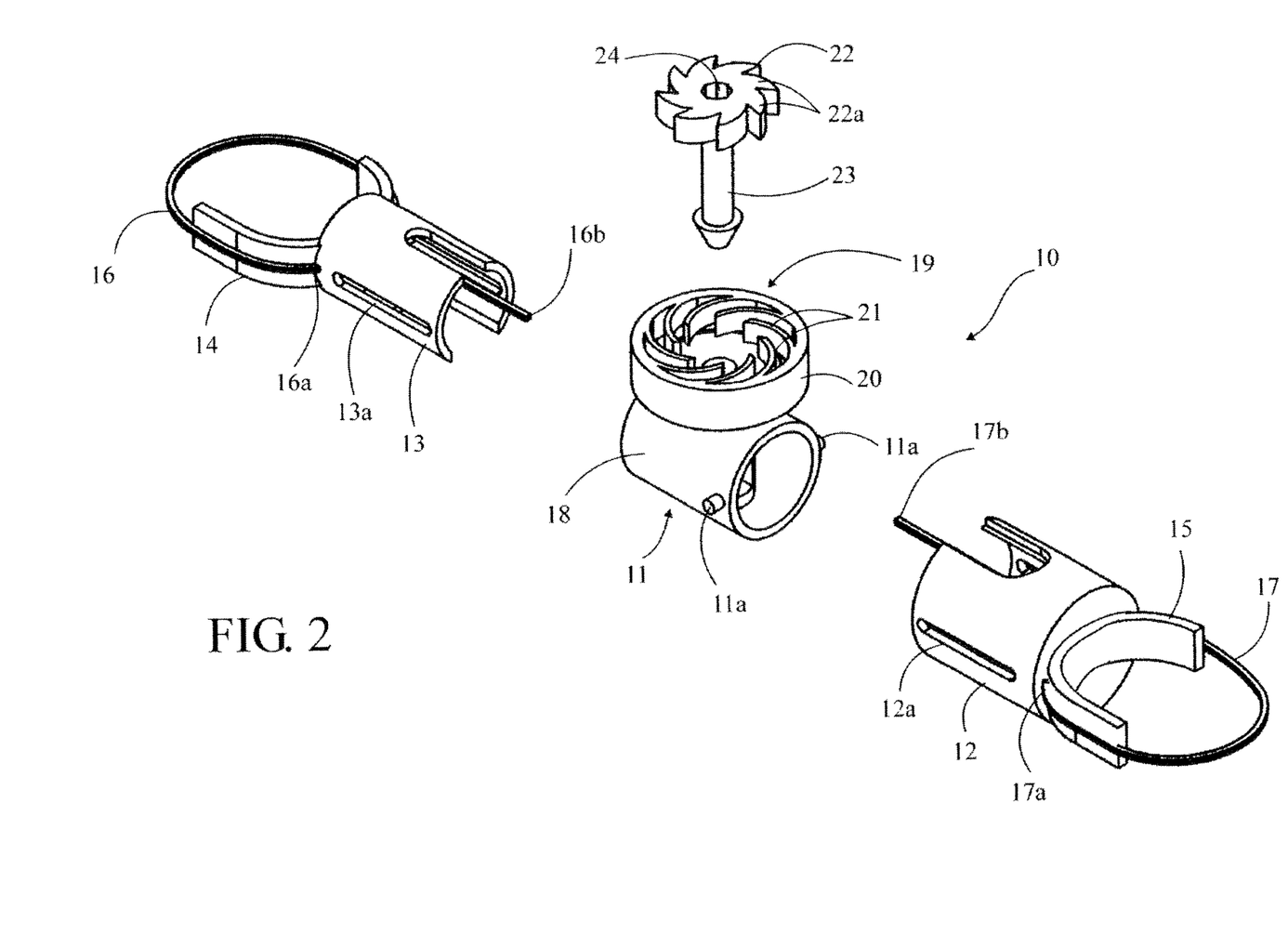
FIG. 2 represents an exploded perspective view of the dental device of FIG. 1.
Figure 3A:
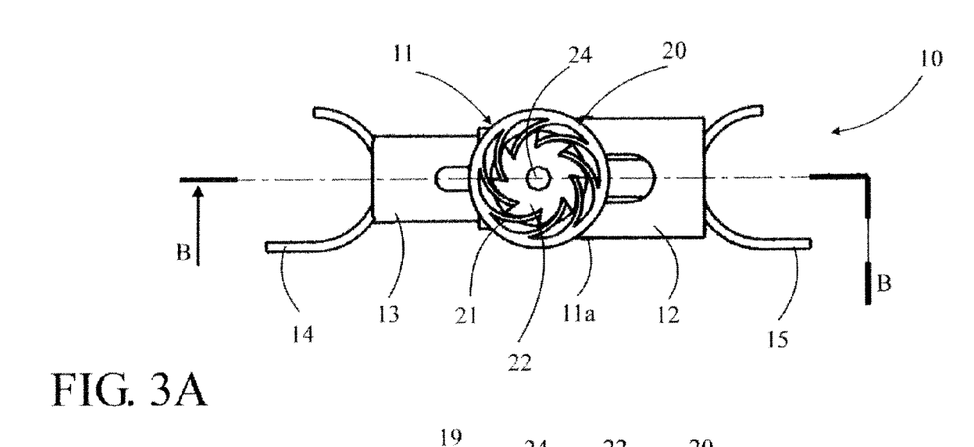
FIG. 3A is a partial top view of the dental device of FIGS. 1 and 2, in its extended position.
Figure 3B:
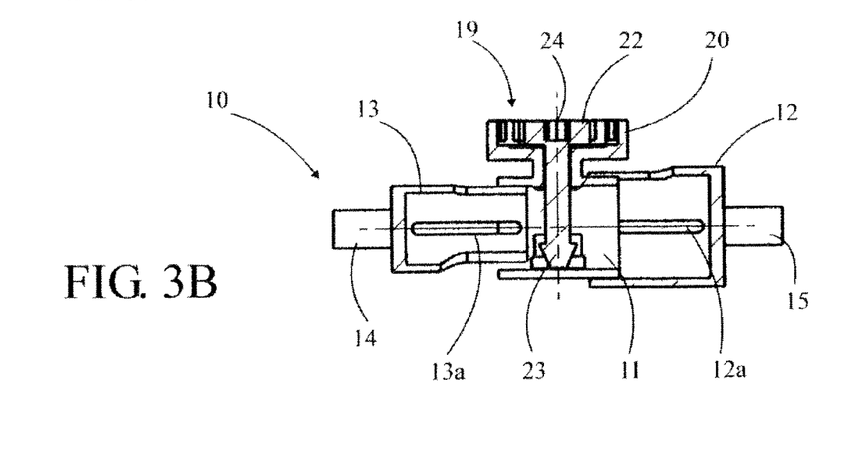
FIG. 3B is a cross-sectional view according to section plane BB of the dental device of FIG. 3A.
Figure 4A:
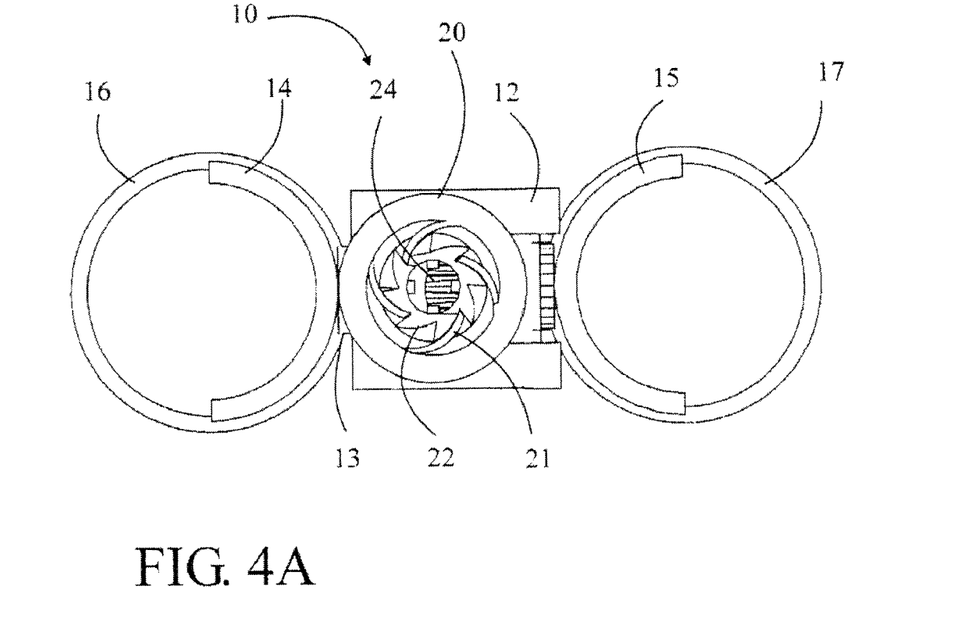
FIG. 4A is a top view of the dental device of FIGS. 1 et 2, in its retracted position.
Figure 4B:
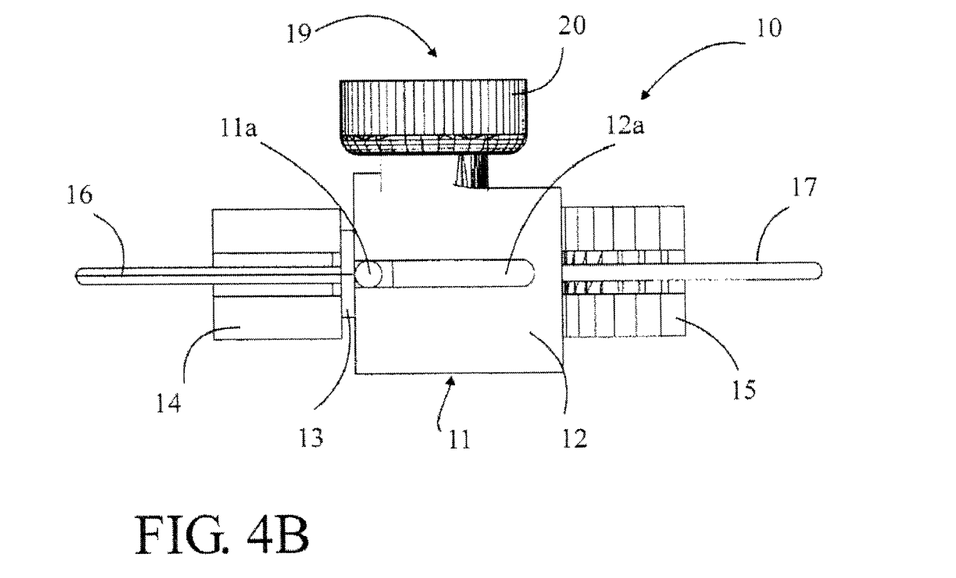
FIG. 4B is a side view of the dental device of FIG. 4A.

Moreover, the central block 11 carries an adjusting mechanism 19 made up of a hollowed ring-shaped part 20 inside of which a certain number of circular arc-shaped elastic blades 21 are mounted, which have the function of pawls cooperating with a toothed wheel 22 fastened firmly on a shaft 23 that extends inside of the tubular element 18 and that can turn only in one direction of rotation thanks to actuating means, which are in the represented example made of a central opening 24 that can receive a hexagonal wrench or a removable knurl (not represented). The combination of the elastic tabs 21 in the form of blades attached to the internal wall of the ring-shaped part 20 and of the central toothed wheel 22 makes up a reverse-lock device of the ratchet type, whose use will be described hereafter.

The straps 16, 17 are flexible and for example made out of fiberglass or similar in order to adapt easily to any tooth profile. The strap 16 has a fixed end 16a attached to the corresponding arm 13 and a fixed end 16b arranged so as to be rolled up on the shaft 23. Similarly, the strap 17 has a fixed end 17a attached to the corresponding arm 12 and a fixed end 17b arranged so as to be rolled up on the shaft 23 (cf. FIG. 2). This way, when the user turns the central toothed wheel 22, for example by means of a hexagonal wrench (not represented) that is inserted in the central opening 24 of this central toothed wheel 22, he exerts a traction on the ends 16b and 17b of the straps 16 and 17. Since the ends 16a and 17a of these straps are attached respectively to the arm 13 and 12 and the straps 16 and 17 are loops placed around the adjacent teeth, this traction moves the extensible arms 12 and 13 in the direction of the adjacent teeth until the supports 14 and 15 are pressed against the respective surfaces of these teeth. The reverse-lock device is made of the elastic tabs 21 that cooperate with the teeth 22a of the central toothed wheel 22 and ensure the shaft 23 and consequently the straps 16 and 17 are locked in position. This way, the practitioner can firmly fasten the dental device 10 in the space corresponding to the toothless gap, and this operation can be carried out immediately after the extraction by the practitioner himself without the intervention of a third person such as the dental-prosthesis technician. In practice, the dentist turns the toothed wheel 22 with the wrench (not represented) or with a preferably removable driving knurl, acting as a wrench introduced in the central opening 24, until the locking of the device is sufficient.

To immobilize the device in position, he locks it with a UV ray-photo or chemo-polymerizable composite resin, which is poured in the liquid state in the central block 11 and more precisely in the ring-shaped part 20 forming a housing, and which attaches the elastic tabs 21 and the toothed wheel 22 together.

The dental device 10 installed this way serves as a support for a prosthesis of the bridge type that the dentist will be able to realize by placing a hollow tooth made out of resin or of any other suitable material on this device and cementing it to fasten it. The dental device 10 is connected to the healthy adjacent teeth, which require no previous mutilation. The dentist can put the temporary bridge in place immediately following an extraction. The intervention of the dental prosthesis maker is suppressed. The aesthetic aspect of the patient is preserved. In brief, this device and the method for putting it in place allows saving time, saving money, improving the treatment and preserving the aesthetic aspect of the patient.

Figure 5:
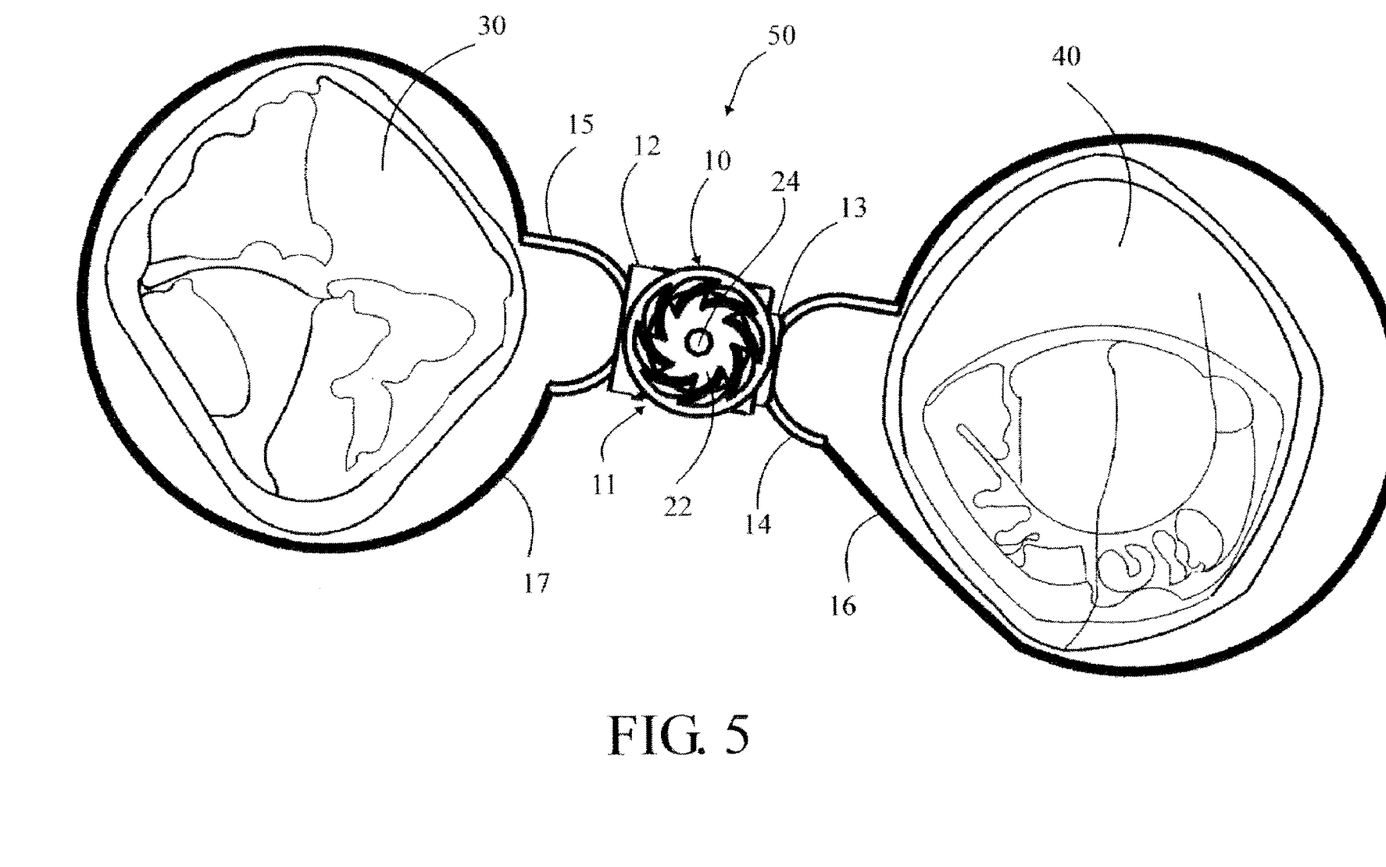
FIG. 5 represents the dental device of FIGS. 1 and 2 at the beginning of its placement in a toothless gap located between two teeth of a patient.
Figure 6:
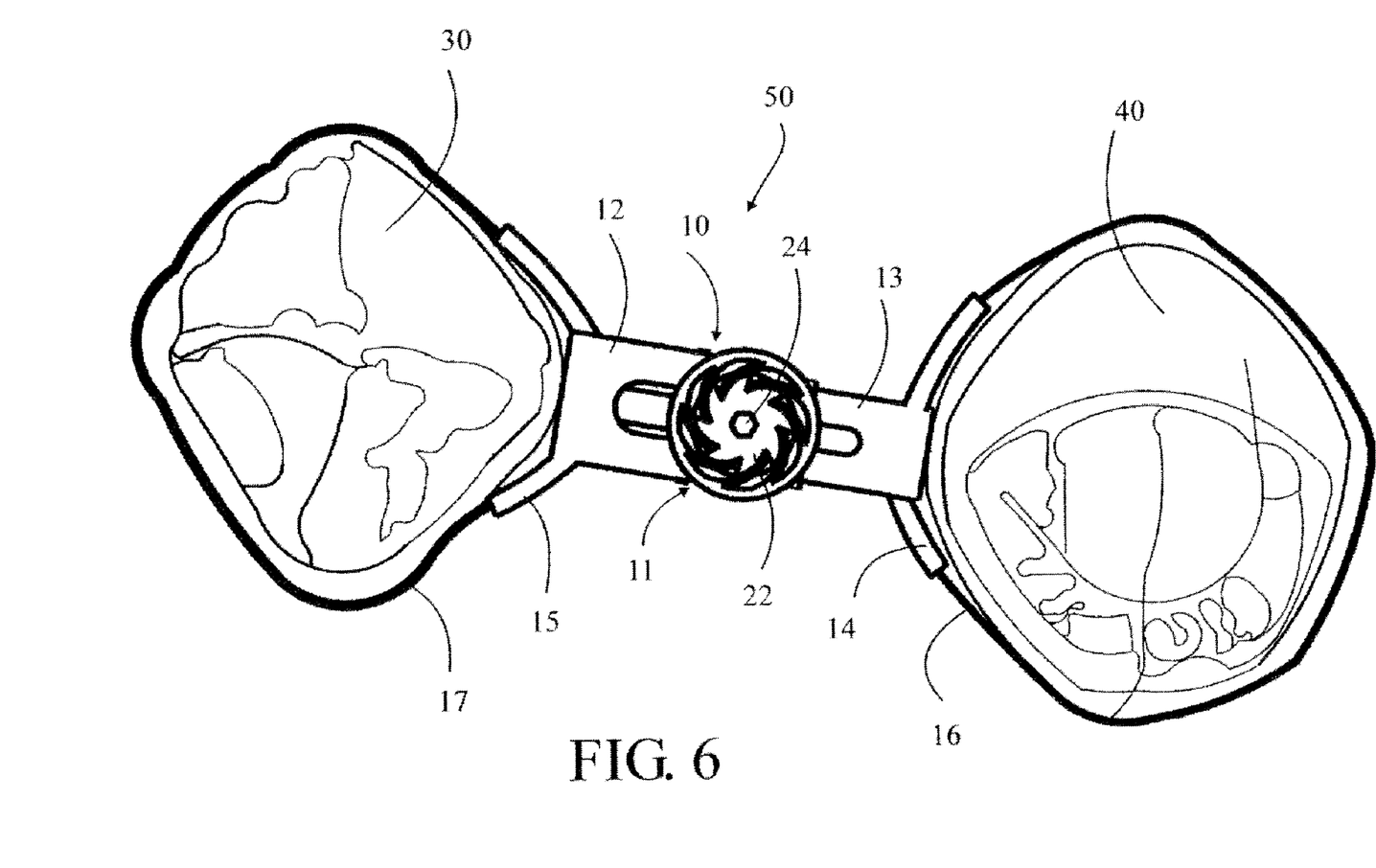
FIG. 6 represents the dental device of FIGS. 1 and 2 after its placement in a toothless gap located between two teeth of a patient.

Putting the device in place is represented by FIGS. 5 and 6. In FIG. 5, two adjacent teeth 30 and 40, which are bordering the toothless gap 50 due to an extraction, are surrounded by the straps 16 and 17. These straps 16 and 17 are greatly larger than the circumference of the two teeth 30 and 40. After this temporary positioning, the operator, generally the dentist, uses a wrench to turn the central toothed wheel 22 of the device 10. This rotation tightens the straps 16 and 17 and pulls both arms 12 and 13 until the supports 14 and 15 come into contact with the adjacent surfaces of the adjacent teeth 30 and 40, as shown in FIG. 6. When the practitioner considers that the tightening is sufficient, he removes the wrench and locks the dental device 10 in position with resin poured in the housing made up by the ring-shaped part 20, this resin being for example polymerized by UV radiation. The dental device 10 is then ready to receive a temporary tooth.

It is well understood that various embodiment variants can be imagined. One of the major operations consists in moving the arms 12 and 13 laterally to bring them from the retracted position to the extended position and in adjusting the straps 16 and 17 around the adjacent teeth 30 and 40 allowing an adaptation in situ to any tooth shape, without cutting in the healthy teeth.

Another way of carrying out the invention:

FIGS. 7 to 10 illustrate an embodiment variant of a dental device 60 according to the invention based on the same technical principle, but with a simplified and more cost-effective design. For simplification purposes, the parts that are identical to those of the embodiment described previously have the same reference numbers.

Figure 7:
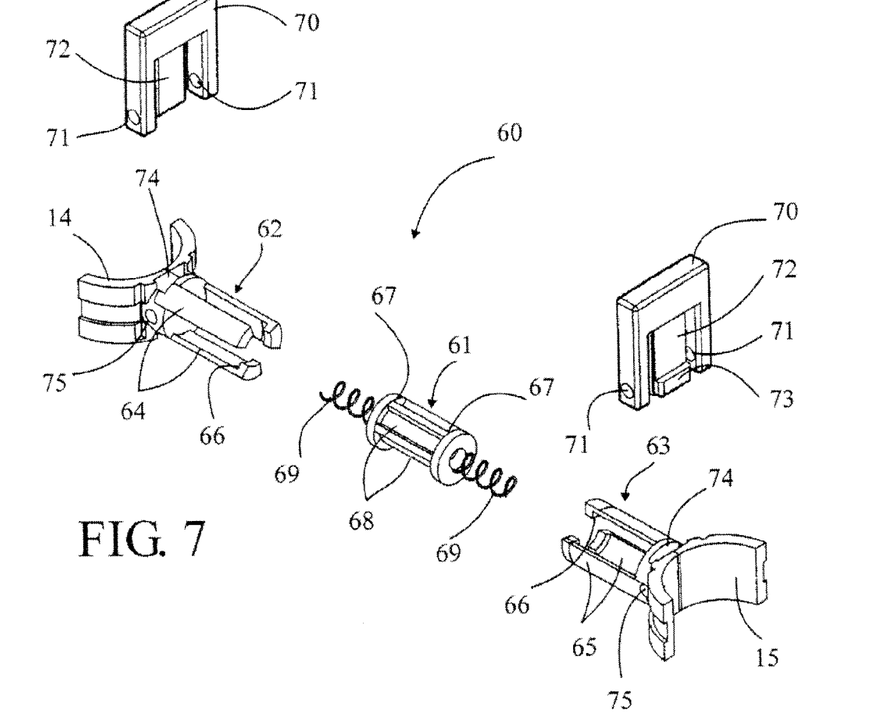
FIG. 7 represents an exploded view of an embodiment variant of the dental device according to the invention.
Figure 8:
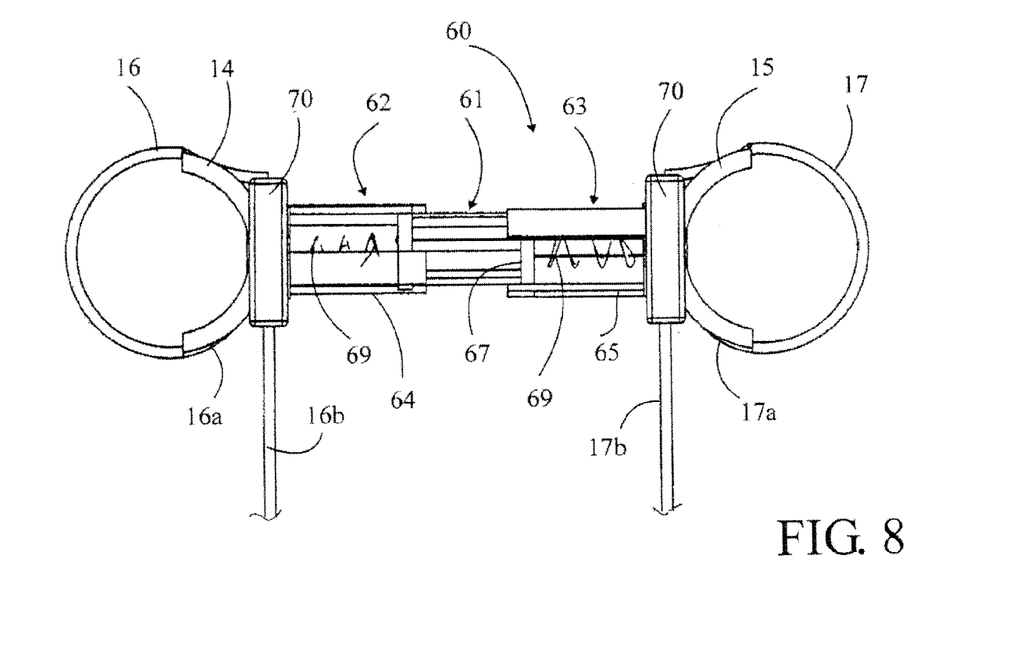
FIG. 8 is a top view of the assembled dental device of FIG. 7.
Figure 9:
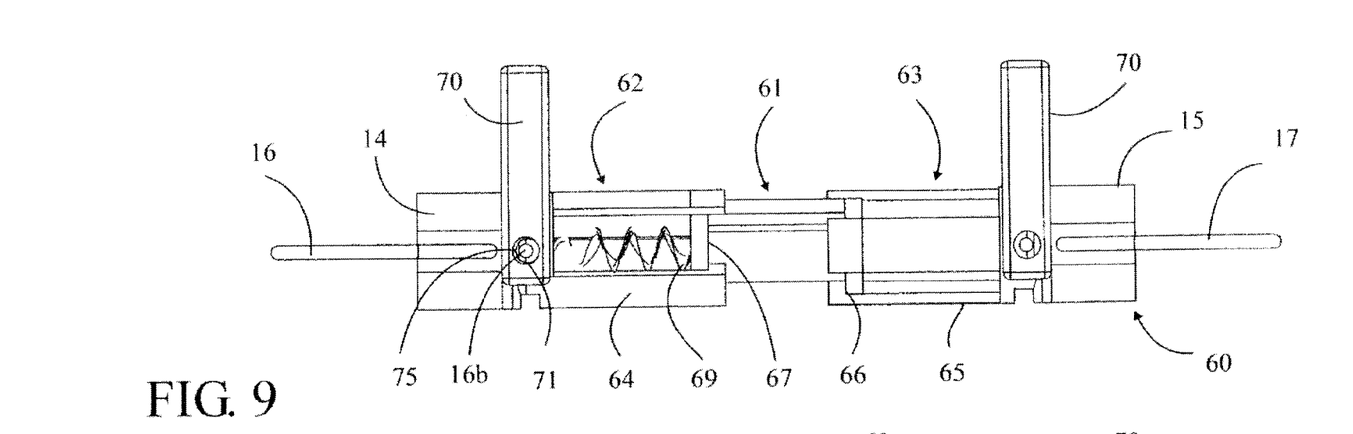
FIG. 9 is a side view of the device of FIG. 7 in its unlocked position.
Figure 10:
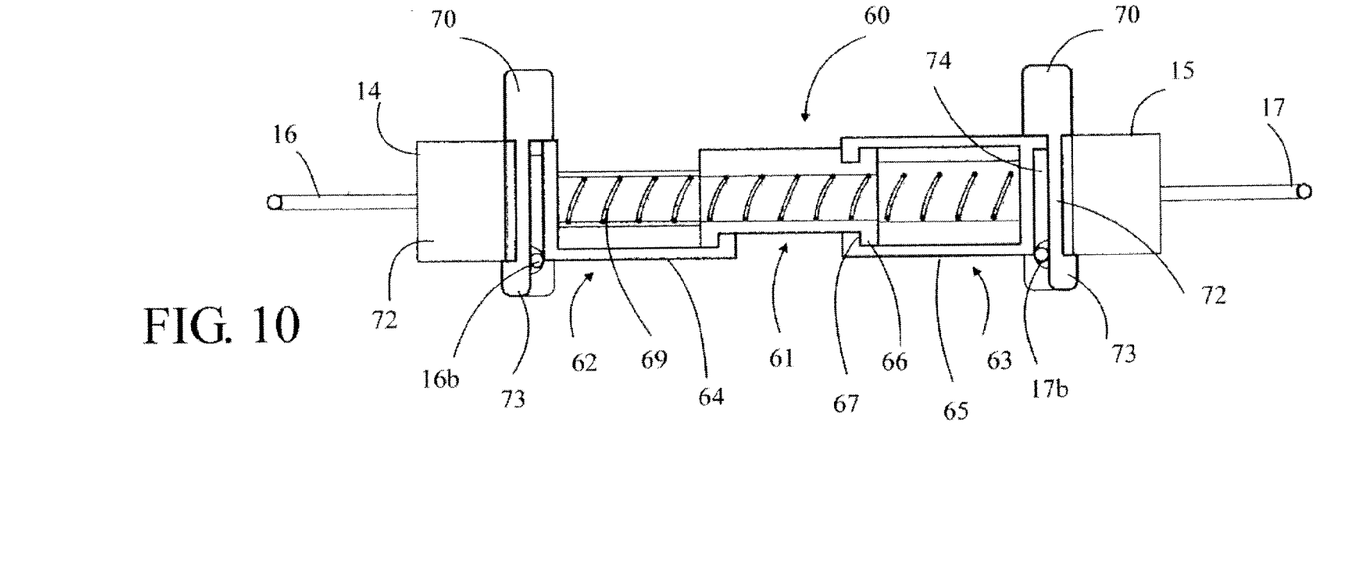
FIG. 10 is a longitudinal cross-sectional view of the of the device of FIG. 9 in its locked position.

This dental device 60 comprises a central block 61 carrying two extensible arms 62 and 63 located opposite to each other, having respectively, at their free end, supports 14 and 15 whose shape is approximately that of cylindrical segments. Two loop-shaped straps 16 and 17 are respectively associated to the two supports 14 and 15, these straps being intended for surrounding the teeth adjacent to a toothless gap. The central block 61 is made of a tubular element arranged to carry the two arms 62 and 63 and to allow them to slide axially for their extension as from a retracted initial position. In this case, the arms 62 and 63 have an internal cross-section approximately equal to the external cross-section of the central block 61 and slide outside of the latter. It is also possible to plan the opposite, that is to say that the arms slide inside of the central block.

In the example represented, the arms 62 and 63 are hollow and made of three parallel and equidistant platelets 64 and 65. Of course, the number, the shape and the arrangement of these platelets may vary. The platelets 64 and 65 have at their free end, shoulders 66 forming axial stops that cooperate with shoulders 67 provided at each end of the central block 61. The central block 61 comprises, in correspondence with platelets 64 and 65, grooves 68 for guiding the arms 62 and 63, which are angularly shifted by one platelet.

Furthermore, the central block 61 carries an adjusting mechanism 69 made up of at least one return element such as a helical spring or similar. This return element 69 is housed inside of the hollow central block 61 and extends inside of the arms 62 and 63 between the supports 14 and 15. In the idle state, this return element 69 automatically exerts a force on the arms 62 and 63 (cf. FIG. 10), which cannot slip out of the central block 61 because of the axial stops formed by the shoulders 66 and 67, towards their extended position. This return element may be replaced with two return elements located opposite to each other or by any equivalent means.

As in the previous example, the straps 16, 17 are flexible and made for example out of fiberglass, or similar, to enable adapting them easily to any tooth profile. Each strap 16, 17 has a fixed end 16a, 17a attached to the corresponding arm 62, 63, and a free end 16b, 17b that passes through the corresponding arm 62, 63 through radial openings 75 so as to be able to slide freely and adapt itself to the periphery of the tooth by pulling manually the free end 16b, 17b of each strap 16, 17. A locking mechanism allows locking the corresponding strap 16, 17 in position when it is adjusted and tightened around a tooth, blocking simultaneously the arms 62, 63 in extended position. It comprises at least one locking element 70 that cooperates with each of the arms 62, 63. In the example shown, each locking element 70 has a reversed U-bracket shape and comprises in the area of the end of its legs, an opening 71 arranged to be crossed by the free end 16b, 17b of the corresponding strap 16, 17. This locking element 70 comprises between its legs a locking tab 72 having at its free end a clip 73 forming a latch. Each arm 62, 63 comprises between its platelets 64 and 65 and its respective support 14, 15 a through opening 74 arranged to receive the locking tab 72 of a locking element 70, and radial openings 75 arranged to receive the free end 16b, 17b of the corresponding strap 16, 17. Of course, any other equivalent blocking or locking element can be suitable.

To introduce the free end 16b, 17b of each strap 16, 17, each locking element 70 is fitted on the corresponding arm 62, 63 by introducing the locking tab 72 in the opening 74 in order to align the openings 71 and the openings 75. The dental device 60 is ready. To put it in place in a toothless gap between two adjacent teeth, the return element 69 is compressed to bring the arms 62, 63 close together, the straps 16, 17 are placed around the teeth adjacent to the toothless gap and the arms 62, 63 are released to allow the supports 14 and 15 to position on the adjacent teeth. Then, the free end 16b, 17b of each strap 16, 17 is pulled to adjust each strap to the corresponding tooth. Then, each strap 16, 17 is locked by pressing each locking element 70 in the opening 74 until the clip 73 at the end of the locking tab 72 comes out of the opening 74 and locks outside of the arm 62, 63, pinching the strap 16, 17 between the locking tab 72 and the openings 71, 75 to block it.

As in the previous example, the practitioner is able to fasten firmly the dental device 60 in the space corresponding to the toothless gap. This operation can be carried out immediately, in a simple and quick way, after the extraction by the practitioner himself, without the intervention of a third person. To immobilise the device in position, he blocks it with for example UV ray-photo or chemo-polymerisable composite resin, which is poured in the liquid state on the central block 61 and on the arms 62, 63.

The invention claimed is:

1. A dental device (10, 60) for allowing temporarily filling of a toothless gap (50) following extraction of a tooth, the dental device being arranged so as to be placed in a space located between two adjacent teeth (30, 40) bordering the toothless gap, the dental device comprising:

a central block (11, 61) with two arms (12, 13; 62, 63) located opposite to one another, and the two arms (12, 13; 62, 63) being movable between a retracted position and an extended position;

each of the two arms carrying at least one support (14, 15), at their free end thereof, that is adapted for respectively resting on a surface of one of the two adjacent teeth when the two arms (12, 13; 62, 63) are in the extended position; and the central block including an adjusting mechanism (19, 69) arranged for moving the two arms (12, 13; 62, 63) into the extended position, and the adjusting mechanism (19, 69) comprises two loop-shaped adjustable straps (16, 17) arranged to surround respectively the adjacent teeth (30, 40) and to bring the two arms (12, 13; 62, 63) in the extended position; and a locking mechanism (21, 22; 70) for locking the straps when the two arms (12, 13; 62, 63) are in the extended position.

2. The dental device according to claim 1, wherein the adjusting mechanism (19) comprises a reverse-lock device (20, 21, 22).

3. The dental device according to claim 1, wherein the reverse-lock device comprises at least one toothed wheel (22) cooperating with pawls (20, 21).

4. The dental device according to claim 3, wherein each of the straps (16, 17) comprises an end (16a, 17a) that is attached to one of the two arms (12, 13) and another end (16b, 17b) attached to a rotary shaft (23) of the adjusting mechanism.

5. The dental device according to claim 4, wherein the rotary shaft (23) of the adjusting mechanism carries a driving means (24) and the toothed wheel (22) of the reverse-lock device.

6. The dental device according to claim 5, wherein the central block (11) comprises a housing (20) which contains the pawls (21) and is arranged to receive the rotary shaft (23).

7. The dental device according to claim 6, wherein the housing (20) is at least partly hollow and arranged to receive either a photo or chemo-polymerizable composite resin in order to lock the adjusting mechanism (19) in position when the arms (12, 13) are in the extended position.

8. The dental device according to claim 1, wherein the adjusting mechanism (69) comprises at least one return element housed in the central block (11) and arranged to exert a force on the two arms (62, 63) toward the extended position.

9. The dental device according to claim 1, wherein each of the straps (16, 17) comprises an end (16a, 17a) that is attached to one of the two arms (62, 63) and another end (16b, 17b) that cooperates with the locking mechanism (70).

10. The dental device according to claim 9, wherein the locking mechanism comprises at least one locking element (70) that cooperates with each of the two arms (62, 63) in order to lock the corresponding strap (16, 17) by pinching the corresponding strap (16, 17) between the arm and the locking element.

11. The dental device according to claim 10, wherein the locking element (70) comprises at least one locking tab (72) arranged to lock on the corresponding arm (62, 63).

12. The dental device according to claim 1, wherein the straps (16, 17) are flexible and made of glass fibre.

13. The dental device according to claim 1, wherein each of the straps (16, 17) comprises an end (16a, 17a) that is fixedly attached to a respective one of the two arms (62, 63) and another end (16b, 17b) that is adjustably securable with respect to the respective one of the two arms (62, 63) to facilitate surrounding different size teeth.

14. The dental device according to claim 1, wherein the central block (11, 61) has only two arms (12, 13; 62, 63).

15. The dental device according to claim 1, wherein the straps (16, 17) and the at least one supports (14, 15) of the two arms (12, 13; 62, 63) define loops which surround respectively the adjacent teeth (30, 40), and the straps (16, 17) are adjustable to adjust respective circumferences of the loops.

16. A method of using a dental device (10, 60) for temporarily filling a toothless gap (50) following extraction of a tooth, the device being arranged so as to be located in a space between two adjacent teeth (30, 40) bordering the toothless gap, the dental device comprising a central block (11, 61) and two arms (12, 13; 62, 63) opposite located on opposite ends of the central block (11, 61), and two arms (12, 13; 62, 63) being extendible between a retracted position and an extended position, each of the two arms carrying at least one support (14, 15), at their free end thereof, that is adapted for respectively resting on a surface of the adjacent teeth when the two arms are in the extended position, and the central block including an adjusting mechanism (19, 69) arranged for moving the two arms into the extended position, the adjusting mechanism (19, 69) comprises two loop-shaped straps (16, 17) arranged to surround respectively the adjacent teeth (30, 40) when the two arms (12, 13; 62, 63) are in the extended position, and a locking means (21, 22; 70) for the adjusting mechanism when the two arms are in the extended position, the method comprising the steps of:

positioning the dental device (10, 60) between the two adjacent teeth that border the toothless gap;

positioning each one of the straps (16, 17) around a respective one of the two adjacent teeth; and actuating the adjusting mechanism (19, 69) to extend the two arms (12, 13; 62, 63) until the respective supports (14, 15) contact with adjacent surfaces of the two adjacent teeth to tighten the straps (16, 17) around the teeth.

17. The method according to claim 16, further comprising the step of locking the dental device (10, 60) in position, once the tightening is considered sufficient, with either a photo or chemo-polymerizable composite resin for locking the adjusting mechanism (19, 69).

18. A dental device (10, 60) for temporarily filling a toothless gap (50) between two adjacent teeth (30, 40) following extraction of a tooth, the device (10, 60) comprising:

a central block (11, 61) sized for positioning within the toothless gap and two arms (12, 13; 62, 63), the two arms (12, 13; 62, 63) being arranged on opposite sides of the central block (11, 61) and being extendible from a retracted position to an extended position, each of the two arms (12, 13; 62, 63) comprising a free end, remote from the central block (11, 61), having at least one support (14, 15) that abuts a surface of the respective adjacent tooth (30, 40) when the two arms (12, 13; 62, 63) are in the extended position;

the central block (11, 61) comprises an adjusting mechanism (19, 69) which biases the two arms (12, 13; 62, 63), from the retracted position to the extended position;

the adjusting mechanism (19, 69) comprising two loop-shaped adjustable straps (16, 17), and each of the two loop-shaped adjustable straps (16, 17) surrounding a respective one of the two adjacent teeth (30, 40), when the two arms (12, 13; 62, 63) are in the extended position, and a locking mechanism (21, 22; 70) which locks the adjusting mechanism (19, 69) when the two arms (12, 13; 62, 63) are in the extended position.

* * * * *